United States Patent
Dalgleish et al.

(10) Patent No.: US 11,065,245 B2
(45) Date of Patent: Jul. 20, 2021

(54) PRIMING OF CANCER CELLS WITH LOW DOSE NALTREXONE

(71) Applicant: CANCER VACCINE INSTITUTE, London (GB)

(72) Inventors: Angus Dalgleish, London (GB); Wai Liu, London (GB)

(73) Assignee: Cancer Vaccine Institute, London (GB)

( * ) Notice: Subject to any disclaimer, the term of this patent is extended or adjusted under 35 U.S.C. 154(b) by 92 days.

(21) Appl. No.: 15/317,082

(22) PCT Filed: Jun. 9, 2015

(86) PCT No.: PCT/GB2015/051686
§ 371 (c)(1),
(2) Date: Dec. 7, 2016

(87) PCT Pub. No.: WO2015/189597
PCT Pub. Date: Dec. 17, 2015

(65) Prior Publication Data
US 2017/0119755 A1   May 4, 2017

(30) Foreign Application Priority Data

Jun. 9, 2014 (GB) .................................... 1410216

(51) Int. Cl.
| | | |
|---|---|---|
| *A61K 31/485* | (2006.01) | |
| *A61K 31/436* | (2006.01) | |
| *A61K 31/282* | (2006.01) | |
| *A61K 31/664* | (2006.01) | |
| *A61K 31/7068* | (2006.01) | |
| *A61K 45/06* | (2006.01) | |
| *G01N 33/574* | (2006.01) | |

(52) U.S. Cl.
CPC .......... *A61K 31/485* (2013.01); *A61K 31/282* (2013.01); *A61K 31/436* (2013.01); *A61K 31/664* (2013.01); *A61K 31/7068* (2013.01); *A61K 45/06* (2013.01); *G01N 33/57484* (2013.01); *G01N 2333/4703* (2013.01); *G01N 2510/00* (2013.01)

(58) Field of Classification Search
CPC .............. A61K 31/282; A61K 31/7068; A61K 31/664; A61K 31/485; A61K 31/436; A61K 45/06; G01N 33/57484; G01N 2333/4703; G01N 2510/00
See application file for complete search history.

(56) References Cited

U.S. PATENT DOCUMENTS

| | | | | |
|---|---|---|---|---|
| 9,895,438 B2 * | 2/2018 | Dalgleish | ............... | A61K 45/06 |
| 2018/0207263 A1 * | 7/2018 | Dalgleish | ............... | A61K 45/06 |

FOREIGN PATENT DOCUMENTS

| | | |
|---|---|---|
| WO | 03/037340 A1 | 5/2003 |
| WO | 2009/117669 A2 | 9/2009 |
| WO | 2013/122140 A1 | 8/2013 |

OTHER PUBLICATIONS

Lissoni Paolo et al: "A new neuroimmunotherapeutic strategy of subcutaneous low-dose interleukin-2 plus the long-acting opioid antagonist naltrexone in metastatic cancer patients progressing on interleukin-2 alone", Neuroendocrinology Letters, vol. 23, No. 3, Jun. 1, 2002, pp. 255-258.
Singleton et al: "Synergistic effects of methylnaltrexone with 5-Fluorouracil and bevacizumab on inhibition of vascular endothelial growth factor induced angiogenisis" Mol. Cancer Ther, vol. 7, No. 6, Jun. 2008, pp. 1669-1679.
James Cattell, Written Opinion of the International Searching Authority, European Patent Office, PCT/GB2015/051686.
Donahue RN, et al., "Low-dose naltrexone suppresses ovarian cancer and exhibits enhanced inhibition in combination with cisplatin," Experimental Biology and Medicine, vol. 236, No. 7, p. 883-895, 2011.
Imamura, Akiko, Notice of Reason for Rejection, Japanese Patent Office, JP Appl. No. 2016-572543, dated Apr. 23, 2019.
Wang CZ, et al., "Methylnaltrexone, a peripherally acting opioid receptor antagonist, enhances tumoricidal effects of 5-FU on human carcinoma cells," Anticancer Research, vol. 29, No. 8, p. 2927-2932, 2009.
Hall et al., "Mechanisms of Action of, and Modes of Resistance to, Alkylating Agents Used in the Treatment of Haematological Malignancies," Blood Reviews, 6:163-173, 1992.
Kaye, SB, "New antimetabolites in cancer chemotherapy and their clinical impact," Br. J. of Cancer, 78(3):1-7, 1998.

* cited by examiner

*Primary Examiner* — Lawrence E Crane
(74) *Attorney, Agent, or Firm* — Gavrilovich, Dodd & Lindsey LLP (57) ABSTRACT

The disclosure provides methods of treating a tumor/cancer by administering naltrexone or an analogue thereof, followed by a recovery phase, and then administering a small molecule signaling inhibitor such as PI3-kinase inhibitors, AKT inhibitors, taxanes, antimetabolites, alkylating agents and/or cell cycle inhibitors. The disclosure also provides diagnostic methods for assessing a therapeutic response to the methods of treatment.

13 Claims, 6 Drawing Sheets

PRIMING OF CANCER CELLS WITH LOW DOSE NALTREXONE

CROSS REFERENCE TO RELATED APPLICATIONS

This application is a U.S. National Stage Application filed under 35 U.S.C. § 371 and claims the benefit of International Application No. PCT/GB2015/051686, filed Jun. 9, 2015, which claims priority under 35 U.S.C. § 119 to Great Britain Application No. 1410216.4, filed Jun. 9, 2014, the disclosures of which are incorporated herein by reference.

FIELD OF THE INVENTION

The invention relates to regimes of drug administration and drug combinations for use in the treatment of cancer.

BACKGROUND TO THE INVENTION

Naltrexone is an orally-administered opioid antagonist with the chemical name morphinan-6-one, 17-(cyclopropylmethyl)-4,5-epoxy-3,14-di hydroxy-(5α), which is commonly used as a treatment for opiate addiction. A number of patients, however, use low doses of naltrexone (LDN) as an off-label treatment for a range of immune-related pathologies and cancer. There is preliminary evidence that LDN may be effective in Multiple Sclerosis (Rahn et al. 2011), Crohn's disease (Smith et al. 2011) and certain cancers.

With regard to cancer, Zagon and McLaughlin (1983) and Hytrek et al. (1996) reported LDN-mediated inhibition of murine neuroblastoma and human colon cancer cell growth respectively, when evaluated in murine xenograft models. Furthermore, combinations of LDN with additional therapeutic agents have been found to be effective against the growth and progression of certain cancer types, for example Donahue et al. (2011a) reported potent anti-proliferative effects of LDN and cisplatin on human ovarian cancer cells both in vitro and in an in vivo murine xenograft model. In the clinic, Berkson et al. (2006) described the long term survival of a patient having pancreatic cancer with metastasis to liver, following treatment with α-lipoic acid in combination with LDN; the authors have since reported similar observations in three further patients with metastatic pancreatic cancer (Berkson et al. 2009).

With regard to the mechanism of growth inhibition by naltrexone, Donahue et al. (2011b) reported the anti-proliferative effects of short-term naltrexone exposure in human ovarian cancer cells to be related to a decrease in DNA synthesis, dependent on p16 and/or p21 cyclin-dependent inhibitory kinase pathways. The authors did not report any alterations, resulting from this exposure, in pathways relating to cell survival (necrosis and apoptosis). The mechanism underlying the anti-proliferative effects of naltrexone, in particular LDN, is therefore largely still to be explored. Accordingly, rational therapeutic strategies derived from a greater mechanistic understanding of LDN are still to be developed.

SUMMARY OF THE INVENTION

It has been found by the present inventors that, firstly, the efficacy of low dose naltrexone (LDN), when used to inhibit the growth of cells of a tumour/cancer, is heightened though the use of a recovery (or wash) phase following administration (Example 1). Secondly, the present inventors have determined LDN to have specific effects with regard to the levels of cellular proteins with a role in the regulation of apoptosis (inter alia, Bcl-2-associated death promoter (BAD) protein and serine/threonine specific kinases such as AKT, also known as protein kinase B) (Example 2).

The above properties of LDN, previously unknown in the art, indicate that specific regimes of administration when used in combination with small molecule signalling inhibitors (which feed into the pathways found to be mediated by LDN), will maximise the drug's pro-apoptotic and therefore anti-tumourigenic potential. Thus, LDN is to be used to prime the cells of a tumour/cancer (a first treatment phase) prior to intervention with a small molecule signalling inhibitor selected from the group consisting of PI3-kinase inhibitors, AKT inhibitors, taxanes, antimetabolites, alkylating agents and cell cycle inhibitors (a second treatment phase).

Priming with LDN as part of a first treatment phase, before intervention with exemplary small molecular signalling inhibitors, is demonstrated in Example 3. It has been shown by the present inventors that said priming results in greater cell kill than both administration of the inhibitor following a phase without treatment (in which no LDN is administered), and also continuous LDN administration. Said priming with LDN is to be made more effective by the use of an intervening recovery phase (as detailed above), in which there is no administration of either LDN or the small molecule signalling inhibitor.

According to a first aspect of the invention, there is provided a pharmaceutical composition comprising naltrexone or an analogue thereof for use in the treatment of a subject having a tumour/cancer; wherein the naltrexone or the analogue thereof is to be administered to the subject in a first treatment phase, followed by a recovery phase; wherein, following the recovery phase, a small molecule signalling inhibitor selected from the group consisting of PI3-kinase inhibitors, AKT inhibitors, taxanes, antimetabolites, alkylating agents and cell cycle inhibitors is to be administered to the subject in a second treatment phase; the recovery phase being characterised by the absence of administration of the naltrexone or the analogue thereof and the small molecule signalling inhibitor.

According to a second aspect of the invention, there is provided a diagnostic test for monitoring the response of a subject having a tumour/cancer to a first treatment phase in which the subject is administered naltrexone or an analogue thereof; comprising analysing a sample obtained from the subject who is, or has been, undergoing said first treatment phase, to determine whether:

(a) BAD protein is upregulated and/or phosphorylated AKT protein is downregulated,
(b) BAD protein is substantially localised to the mitochondria, and/or
(c) BAD protein is not substantially in a phosphorylated state wherein, if they are, there is a positive indication of the subject to be suitable to undertake a second treatment phase, comprising administration of a small molecule signalling inhibitor selected from the group consisting of PI3-kinase inhibitors, AKT inhibitors, taxanes, antimetabolites, alkylating agents and cell cycle inhibitors.

According to a third aspect of the invention, there is provided an in vitro method of testing a small molecule signalling inhibitor for efficacy in the treatment of a tumour/cancer when for use in combination with naltrexone or an analogue thereof; comprising administering the small molecule signalling inhibitor, selected from the group consisting of PI3-kinase inhibitors, AKT inhibitors, taxanes, antimetabolites, alkylating agents and cell cycle inhibitors, concurrently with and/or after the naltrexone or the analogue thereof to cells of the tumour/cancer, and analysing a sample comprising one or more of said cells to determine whether:
(a) BAD protein is upregulated and/or phosphorylated AKT protein is downregulated,
(b) BAD protein is substantially localised to the mitochondria, and/or
(c) BAD protein is not substantially in a phosphorylated state;
wherein, if they are, there is a positive indication of the efficacy of the small molecule signalling inhibitor.

According to a fourth aspect of the invention, there is provided a pharmaceutical composition comprising naltrexone or an analogue thereof, for use in a method of testing a small molecule signalling inhibitor for efficacy in the treatment of a tumour/cancer when to be used in combination with the naltrexone or the analogue thereof, said method comprising administering the small molecule signalling inhibitor, selected from the group consisting of PI3-kinase inhibitors, AKT inhibitors, taxanes, antimetabolites, alkylating agents and cell cycle inhibitors, concurrently with and/or after the naltrexone or the analogue thereof to a subject having a tumour/cancer, and analysing a sample comprising one or more cells of the tumour/cancer to determine whether:
(a) BAD protein is upregulated and/or phosphorylated AKT protein is downregulated,
(b) BAD protein is substantially localised to the mitochondria, and/or
(c) BAD protein is not substantially in a phosphorylated state;
wherein, if they are, there is a positive indication of the efficacy of the small molecule signalling inhibitor agent.

BRIEF DESCRIPTION OF THE FIGURES

FIG. 1 shows a recovery phase following LDN exposure causing a reduction in cell numbers. (A) A549 cells (a lung cancer cell line) and (B) HCT116 cells (a colorectal carcinoma cell line), were cultured for 48 h in 1 nM and 10 nM (low dose) naltrexone (LDN) and in 1 µM and 10 µM (standard dose) naltrexone (NTX). Cells were either then washed and allowed to grow in drug-free medium for 24 h (wash) or continuously cultured in naltrexone for a total of 72 h (72); cell was viability assessed by absorbance readings. Effect of the wash step on HCT116 cells were also measured by (C) 3-(4,5-dimethylthiazol-2-yl)-2,5-diphenyltetrazolium bromide (MTT) colorimetric assay, (D) cell counting and (E) percentage of viable cells.

FIG. 3 shows the effects of naltrexone at 10 µM (NTX) and 10 nM (LDN) in HCT116 cells, relative to untreated cells, on levels of a number of cell cycle proteins as assessed by (A) western blot, and (B) densitometry analysis of protein bands in (A). Methodologically, HCT116 cells were treated with NTX and LDN for 48 h before determination of cellular proteins as labelled in the figure. The intensities of each of the bands indicate the level at which these proteins were expressed, which were enumerated by density analysis.

FIG. 4 compares (A) gene expression levels of the above cell cycle proteins (following NTX and LDN treatment), as measured by microarray analysis with (B) protein levels shown in FIG. 3(B).

FIG. 5 demonstrates the effects of the treatment regimens detailed in Example 3 on (A) cell numbers and (B) cell viability of HCT116 cells. U-U: untreated for 96 h; L-L: LDN for 96 h; U-C: untreated for 48 h then cyclophosphamide for 48 h; L-C: LDN for 48 h then cyclophosphamide for 48 h; U-G: untreated for 48 h then gemcitabine for 48 h; L-G: LDN for 48 h then gemcitabine for 48 h; U-O: untreated for 48 h then oxaliplatin for 48 h; L-O: LDN for 48 h then oxaliplatin for 48 h.

DETAILED DESCRIPTION OF THE INVENTION

The invention provides novel uses of LDN in the treatment of a subject having a tumour/cancer. In addition, there is provided a diagnostic test so as to assess the response of a subject to priming with LDN. Furthermore, a method of testing the efficacy of a small molecule signalling inhibitor in vitro, when to be used in combination with LDN, is also envisaged.

Figure 1A:
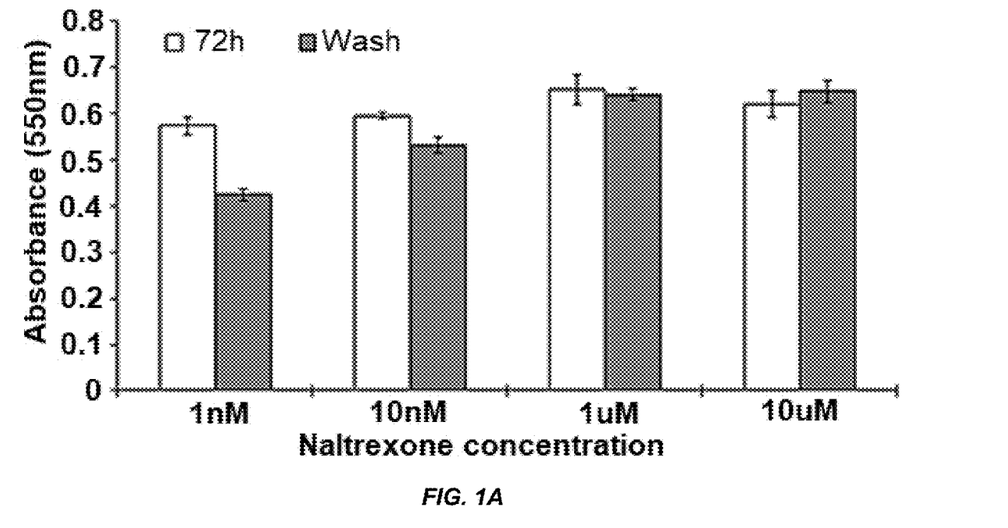
Figure 1B:
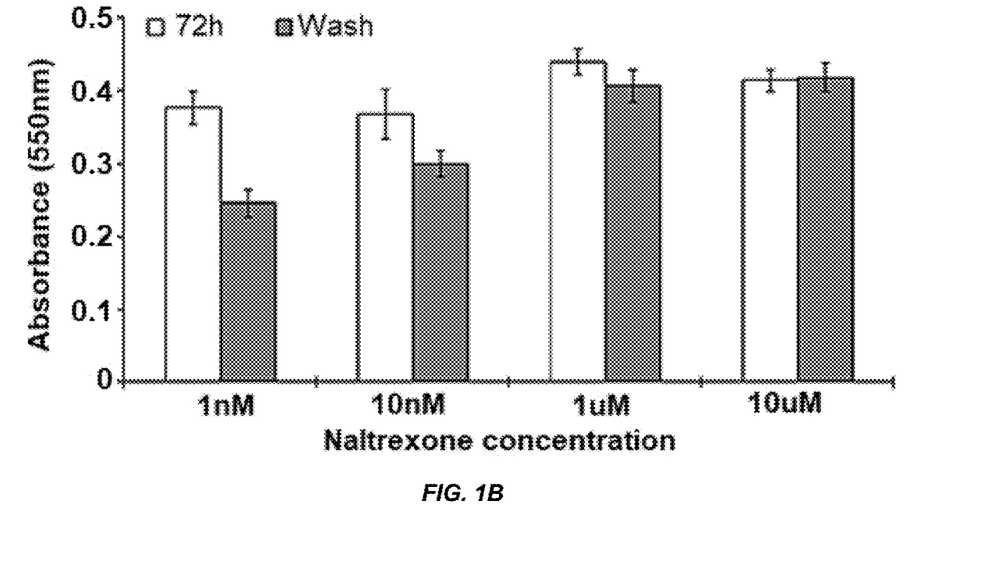
Figure 1C:
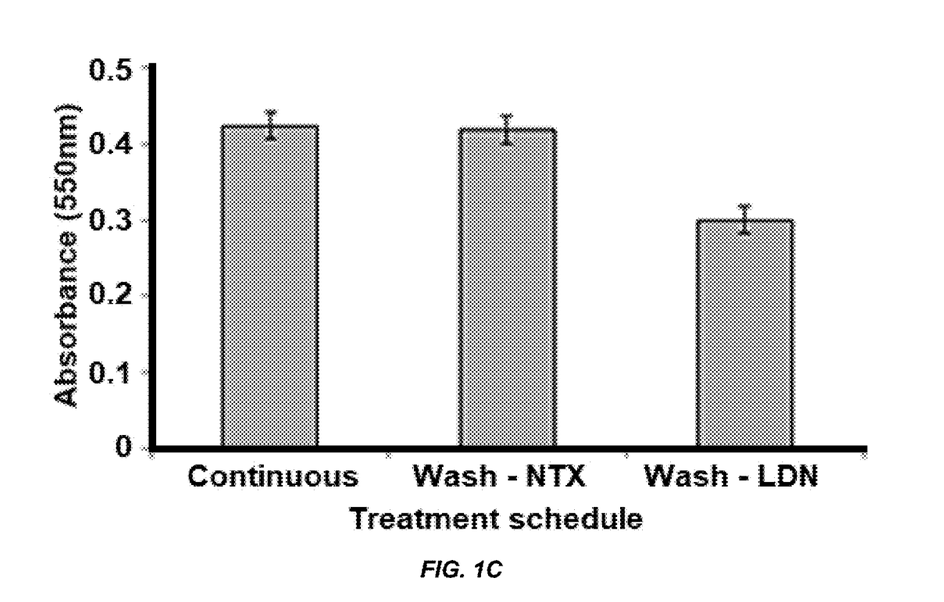
Figure 1D:
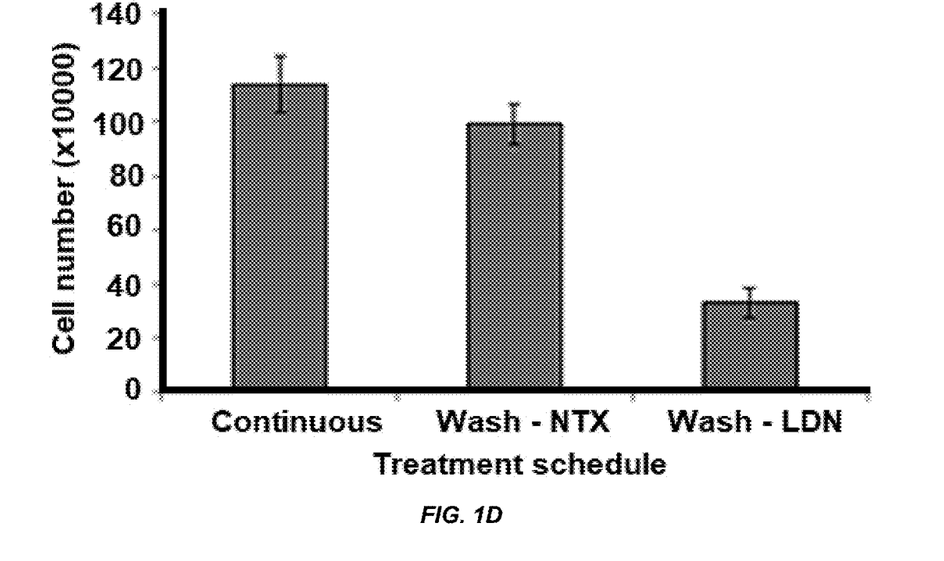
Figure 1E:
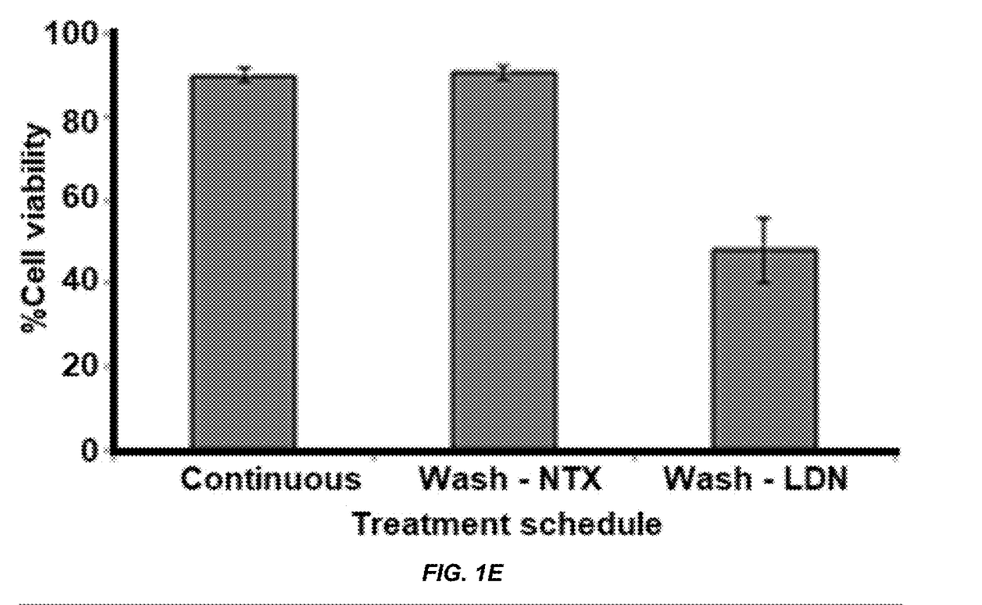
Figure 2:
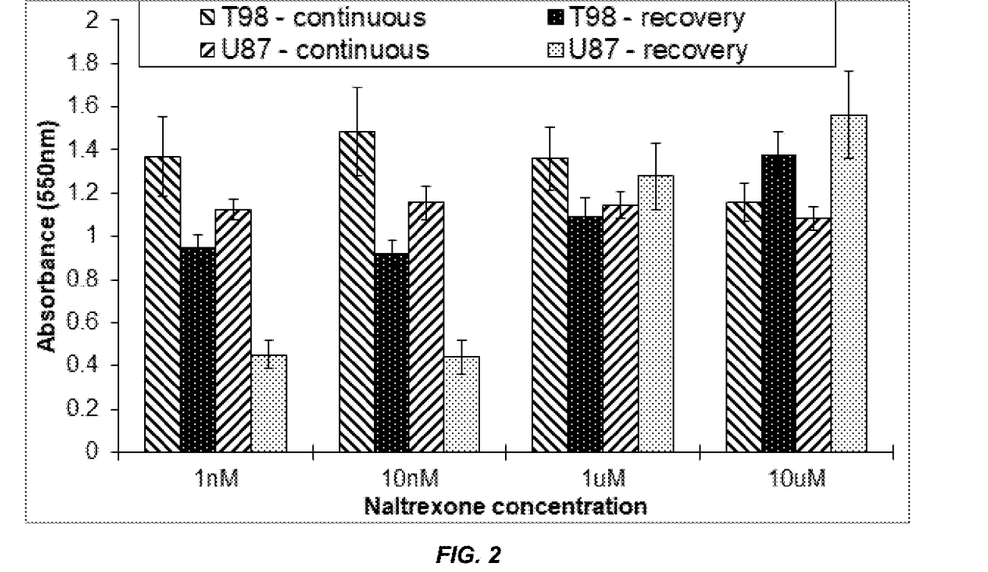
FIG. 2 shows the above effects for T98G and U87MG cells (glioma cell lines), assessed by absorbance readings.
Figure 3A:
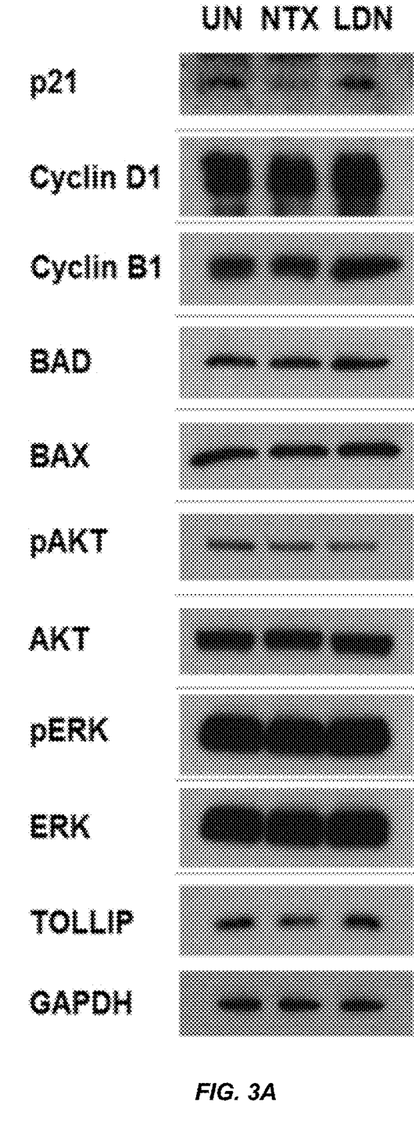
Figure 3B:
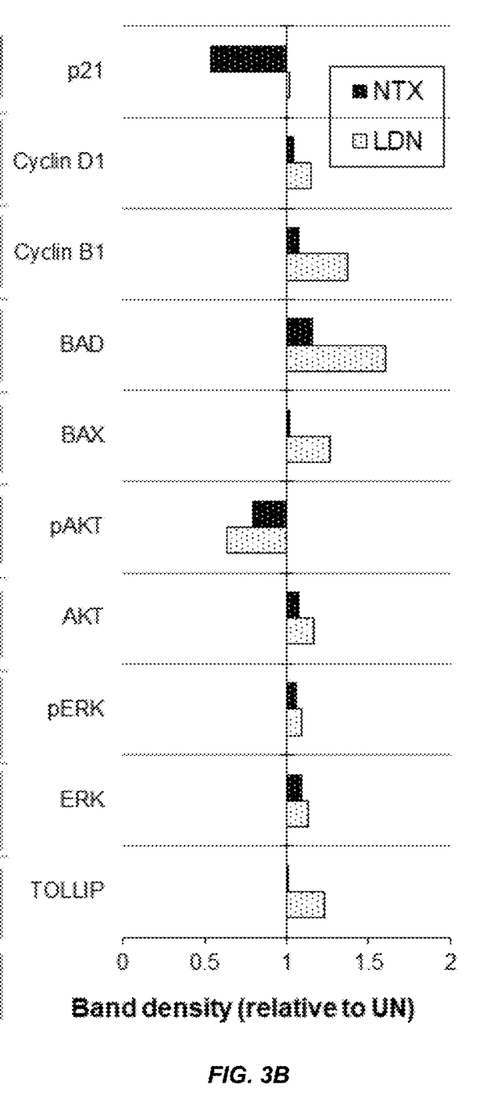
Figure 4A:
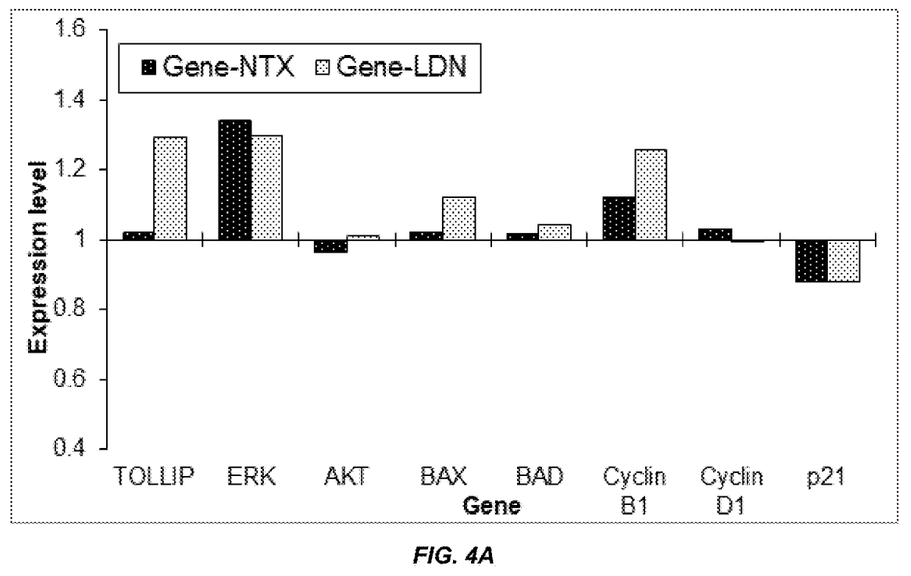
Figure 4B:
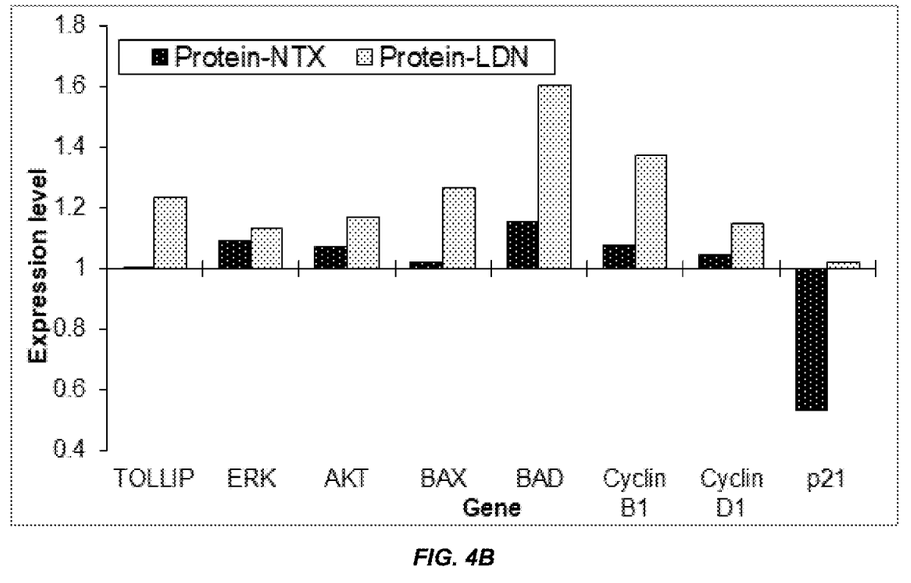

The use of a recovery or wash phase following LDN administration has been found by the present inventors to cause a greater reduction in cell numbers when compared with continuous administration. This is observed for a number of cancer cell lines (Example 1; FIGS. 1 and 2). Moreover, the effects of LDN on the levels of a number of cell cycle proteins have been explored, with the finding that Bcl-2-associated death promoter (BAD) protein is upregulated and phosphorylated AKT (an inhibitor of BAD) is downregulated following LDN treatment (Example 2; FIGS. 3 and 4). Thus, combining LDN administration with intervention with small molecule signalling inhibitors (as defined herein), which feed into these cell survival-regulating pathways, presents a new rational therapeutic strategy for naltrexone use.

Figure 5A:
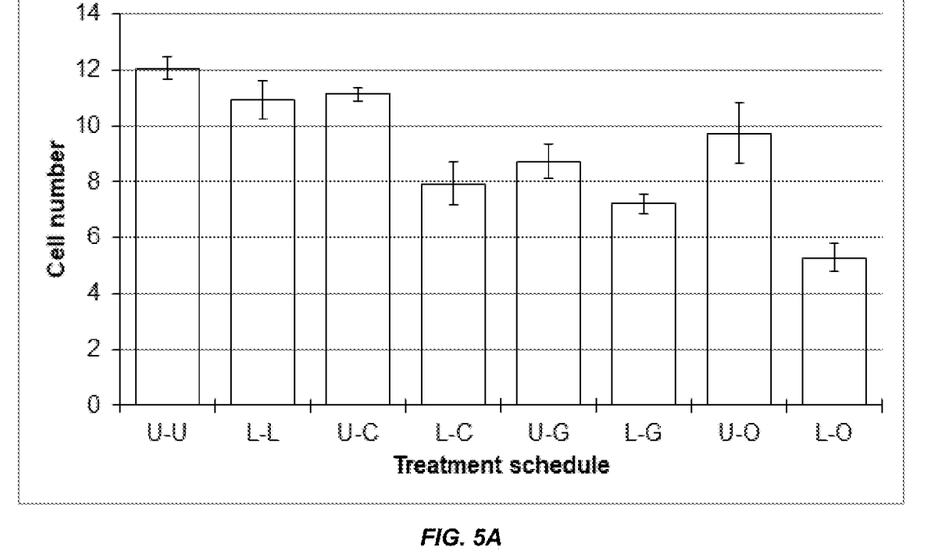
Figure 5B:
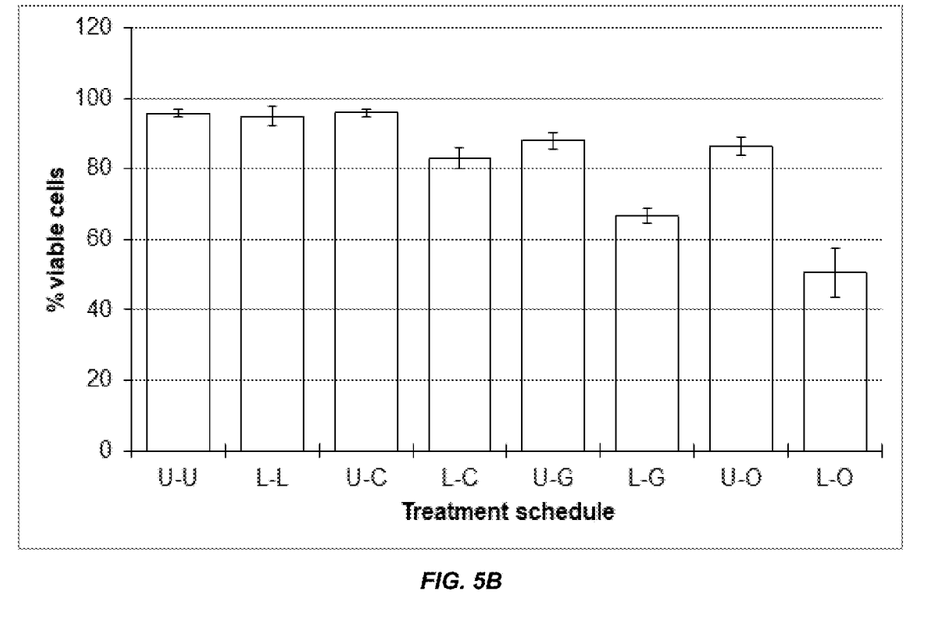

The effects of priming with LDN are demonstrated in Example 3. HCT-116 cells (colorectal carcinoma) administered LDN for 48 hours, followed by culturing with exemplary antimetabolites and alkylating agents for a further 48 hours, demonstrate lower cell numbers and viability than in the absence of LDN priming (FIGS. 5A and B; L-C, L-G and L-O vs U-C, U-G and U-O). The cell kill achieved by these regimes is also greater than that of continuous LDN administration (FIGS. 5A and B; L-L). These data are generated using an industry-standard in vitro cell line model of colorectal cancer. However, it is expected that the efficacy of LDN priming in vivo will be greater than that observed with cell lines, due to the immunological effects of the drug (for example, through enhanced cross talk between effector T-cells and professional antigen presenting cells). Without wishing to be bound by theory, LDN may also stall cancer cells at specific stages of the cell cycle (in addition to upregulating pro-apoptotic proteins such as BAD). This may allow the small molecule signalling inhibitor to act on a population of cells which are in an aligned state in the cell cycle, thereby increasing sensitivity.

BAD protein is known to the skilled person, and as used herein, the term has its conventional meaning as used in the art, for example by Danial (2009). Similarly, all other terms used herein to denote proteins that are known in the art have their conventional meanings, as would be understood by the skilled person. BAD belongs to the BH3-only pro-apoptotic protein family, which initiate cell death upon activation, their activity being largely regulated by post-translational modifications which integrate a variety of cell survival or death signals (Danial 2009). BAD specifically promotes apoptosis through the binding and neutralisation of its anti-apoptotic partners BCL-2, BCL-$X_L$ and BCL-W, located in the mitochondria, where BAD translocates (from the cytosol) upon the withdrawal of growth factor survival signals. Phosphorylation of BAD (resulting from upstream survival signals) is inhibitory; this is mediated by specifically three serine residues (S112, S136 and S155). Phosphorylation of the former two sites allows docking with the BAD inhibitor 14-3-3 protein, and phosphorylation at the latter (and the associated negative charge) renders the interactions between BAD and the hydrophobic binding sites of BCL-2, BCL-$X_L$ and BCL-W energetically unfavourable. Accordingly, when phosphorylated, BAD is both bound by 14-3-3 protein and therefore sequestered in the cytosol (thus prevented from translocating to the mitochondria to initiate apoptosis), and prevented from binding to and neutralising its mitochondrial anti-apoptotic target proteins. However, in healthy cells, a portion of phosphorylated BAD can also reside in the mitochondria (Danial et al. 2003).

Inhibitory phosphorylation of BAD is regulated by myriad upstream survival and cell death signals; as such, BAD is at the apex of a number of signalling pathways. BAD-inhibitory activity (through phosphorylation) is demonstrated by, but not limited to, AKT, RSK, S6K, PKA and PIM kinases. Accordingly, a small molecule signalling inhibitor which negatively regulates (with regard to either activity or expression) inter alia, the above kinases, or their upstream activators will complement the anti-proliferative effects of LDN. Concerning the above kinases, AKT is positively regulated by inter alia, PI3-kinase and RAF kinase activity (mediated by growth factor and cytokine-regulated pathways); RSK is positively regulated by inter alia, MAP-kinase activity (mediated by growth factor and cytokine-regulated pathways); PIM is positively regulated by inter alia, STAT protein (mediated by cytokine-regulated pathways); S6K is positively regulated by inter alia, mTOR (mediated by various stimuli including growth factor-mediated pathways and nutrient levels); PKA is positively regulated by inter alia, cyclic AMP levels (mediated by cytokine and G-protein coupled receptor-regulated pathways) (Danial 2009). Accordingly, negative regulation of these upstream proteins or signalling molecules by a small molecule signalling inhibitor will also complement LDN activity.

Without wishing to be bound by theory, it is thought that a recovery phase after LDN treatment allows the cell to re-engage processes of the cell cycle, which are intertwined with those of cell death. Thus, through the recovery phase, cell death is also enhanced Furthermore, the signalling pathways described above are sensitive to the competency of cell cycling dynamics of tumour cells. Cells that are cycling tend to respond better to small molecule signalling inhibitors that interfere with these pathways. Accordingly, a recovery phase allows time for tumour cells to re-engage some aspects of the cell cycling machinery, thus allowing small molecule inhibitors to work more effectively and increase the cytotoxic response.

As used herein "naltrexone" refers to morphinan-6-one, 17-(cyclopropylmethyl)-4,5-epoxy-3,14-dihydroxy-(5α), and pharmaceutically acceptable salts, solvates, hydrates, stereoisomers, clathrates and prodrugs thereof. The use of naloxone, a structural analogue of naltrexone, is within the purview of the invention and is encompassed within the term "analogue" used in the description and the claims. Similarly, methylnaltrexone is also envisaged as a suitable analogue for use in all aspects of the invention. The preferred form of naltrexone is as its hydrochloride salt form.

As used herein, the term "small molecule signalling inhibitor" refers to compounds having a molecular weight of less than 3000 daltons, including, but not limited to, small organic molecules, peptides and peptidomimetics; said compounds having inhibitory or antagonistic activity towards one or more components of one or more cell signalling pathways; said cell signalling pathway(s) being known in the art to mediate cell growth and/or proliferation, including, but not limited to, the process of apoptosis. "Inhibitory" or "antagonistic" activity, with reference to the small molecule signalling inhibitor, refers to the activity of the one or more components of the cell signalling pathway being reduced in the presence of the small molecule signalling inhibitor, when compared with the level of such activity in the absence of said small molecule signalling inhibitor, when measured under otherwise analogous conditions. Said components include, but are not limited to; cell surface receptors (for example, growth factor receptors, cytokine receptors and G-protein-coupled receptors); intracellular enzymes, including membrane-tethered enzymes (for example, kinases, phosphatases and GTPases); and other mediators and downstream effectors of the cell signalling pathway (for example, chaperones, adaptors, scaffolds, microtubules, transcription factors and initiators of translation). Said cell signalling pathways include, but are not limited to, Akt (protein kinase B)-mediated pathways, Integrin-mediated pathways, Jak-STAT-mediated pathways, mitogen-activated protein kinase-mediated pathways, Wnt/β-catenin-mediated pathways, tumour necrosis factor-mediated pathways; said pathways including the upstream regulators thereof. In some instances, the small molecule signalling inhibitor is a compound having the above properties and a molecular weight of less than 1000 daltons, typically less than 500 daltons. Suitable small molecule signalling inhibitors according to the invention are selected from the group consisting of PI3-kinase inhibitors, AKT inhibitors, taxanes, antimetabolites, alkylating agents and cell cycle inhibitors; said classes having their conventional meanings as used in the art. "Cell cycle inhibitor" refers to a compound which is capable of slowing or stopping progression of a cell or cells in one stage of the cell cycle from progressing to the subsequent stage of the cell cycle.

As used herein, the term "inhibitor" has its conventional meaning as used in the art.

As used herein, the terms "upregulation" and "downregulation", with regard to the cellular levels of a protein, refer respectively to greater or lesser levels when compared with basal levels of said protein in untreated and/or unstimulated cells of the same tissue type, measured under otherwise analogous conditions. Greater or lesser cellular levels of the protein are typically, but not necessarily, reflected by a higher or lower cytosolic concentration of the protein, when compared with untreated and/or unstimulated cells. "Upregulation" and "downregulation" respectively encompass, but are not limited to, increased and decreased expression of the protein in question (whether respectively by increased or decreased levels of transcription of target mRNA and/or translation of the polypeptide); however the terms may also respectively encompass decreased and increased sequestration and/or degradation of said protein; combinations of the above effects are also encompassed.

As used herein, the term "subcellular localisation", when considering a protein, refers to the specific localisation, within the volume of a cell, of a substantial proportion of the total quantity of the protein in the cell; more specifically, the term refers to where said substantial proportion is located relative to identifiable cellular organelles, features or compartments including, but not limited to, the plasma membrane, nucleus, mitochondria, endoplasmic reticulum, golgi apparatus and endosomal vesicles. In the above context, "substantially localised" refers to said substantial proportion being located within the volume of, or being proximal to, a given cellular organelle, feature or compartment; "proximal to" encompasses, but is not limited to, the protein having contact with a phospholipid membrane forming an outer perimeter of the organelle, feature or compartment. By way of example and not limitation, when considering a treated and/or stimulated cell, a protein may be considered "substantially localised" to a given cellular organelle, feature or compartment when the quantity of said protein within the volume of, or proximal to, said organelle, feature or compartment is increased when compared with an untreated and/or unstimulated cell (i.e. in a basal state) of the same tissue type, when measured under otherwise analogous conditions; again, "proximal to" encompasses, but is not limited to, the protein having contact with a phospholipid membrane forming an outer perimeter of the organelle, feature or compartment.

As used herein, the terms "phosphorylated" and "phosphorylated state", with respect to BAD protein, refer to one or more phosphate groups being bound to the protein via any suitable residue, for example one or more serine, threonine, tyrosine and/or histidine residues. Enzymatic phosphorylation of BAD protein at residues S112, S136 and/or S155 through the action of upstream kinases, notably AKT, RSK, S6K, PKA and/or PIM kinases, or the absence of such activity, is to be considered in particular. In the above context, BAD protein being "substantially in a phosphorylated state" refers to the phosphorylated state being the predominant form of cellular BAD protein, and thus the cellular activity of BAD protein being substantially inhibited, notably where resulting from the activity of AKT, RSK, S6K, PKA and/or PIM kinases. The protein "not" being substantially in the above state refers to the opposite of the above conditions, wherein the unphosphorylated state of BAD protein is dominant, notably due to the substantial absence of activity of the above kinases.

As used herein, the terms "treating" and "treatment" and "to treat" refer to both 1) therapeutic measures that cure, slow down, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In some instances, a subject is successfully "treated" for a tumour/cancer according to the present invention if the subject shows one or more of the following: a reduction in the number of, or complete absence of, cancer cells; a reduction in the tumour size; inhibition of, or an absence of, cancer cell infiltration into peripheral organs including, for example, the spread of cancer into soft tissue and bone; inhibition of, or an absence of, tumour metastasis; inhibition of, or an absence of, tumour growth; reduced morbidity and mortality; reduction in tumourigenicity, tumourigenic frequency, or tumourigenic capacity of a tumour; reduction in the number or frequency of cancer stem cells in a tumour; differentiation of tumourigenic cells to a non-tumourigenic state; or some combination of effects.

As used herein, the term "tumour/cancer" refers to any mass of tissue that results from excessive cell growth, proliferation and/or survival, either benign (noncancerous) or malignant (cancerous), including pre-cancerous lesions. The terms "tumour/cancer" and "neoplasm" may be used interchangeably.

As used herein, the term "tumourigenic" refers to the functional features of a solid tumour stem cell including the properties of self-renewal (giving rise to additional tumourigenic cancer stem cells) and proliferation to generate all other tumour cells (giving rise to differentiated and thus non-tumourigenic tumour cells) that allow solid tumour stem cells to form a tumour.

As used herein, the term "subject" refers to any animal (for example, a mammal), including, but not limited to, humans, non-human primates, canines, felines, rodents, and the like, which is to be the recipient of a treatment in which LDN is to be used according to the present invention. Typically, the terms "subject" and "patient" are used interchangeably herein in reference to a human subject.

According to a first aspect of the invention, there is provided a pharmaceutical composition comprising naltrexone or an analogue thereof for use in the treatment of a subject having a tumour/cancer; wherein the naltrexone or the analogue thereof is to be administered to the subject in a first treatment phase, followed by a recovery phase; wherein, following the recovery phase, a small molecule signalling inhibitor selected from the group consisting of PI3-kinase inhibitors, AKT inhibitors, taxanes, antimetabolites, alkylating agents and cell cycle inhibitors is to be administered to the subject in a second treatment phase; the recovery phase being characterised by the absence of administration of the naltrexone or the analogue thereof and the small molecule signalling inhibitor.

According to said first aspect, preferably the naltrexone or the analogue thereof is to be administered in the first treatment phase to the subject at a "low" dose, less than 0.5 mg/kg, preferably less than 0.2 mg/kg, more preferably between 0.01 mg/kg and 0.08 mg/kg, even more preferably between 0.03 mg/kg and 0.06 mg/kg, most preferably between 0.04 mg/kg and 0.05 mg/kg. The composition can be administered in any conventional way. Administration can be by oral or parenteral administration, preferably oral administration. However, other routes of administration are also envisaged. Said first treatment phase is preferably for administration for between 1 and 7 days, more preferably between 1 and 4 days, most preferably between 1 and 2 days; "day" meaning a continuous period of 24 hours. Naltrexone is preferably administered daily (at the above doses) during the first treatment phase. Said recovery phase, in which there is no administration of either the naltrexone (or the analogue thereof) or the small molecule signalling inhibitor is for preferably at least 1 day, and more preferably at least 2 days. Alternatively, the recovery phase may be between 24 and 48 hours, 24 and 36 hours, or 24 and 30 hours. The features of said second treatment phase are dependent on the small molecule signalling inhibitor to be used, however administration is preferably daily, for at least 1 day.

Further according to said first aspect, preferably the small molecule signalling inhibitor is selected from the group consisting of antimetabolites and alkylating agents. The small molecule signalling inhibitor can be administered in any conventional way, the method of administration being largely dependent on the small molecule signalling inhibitor to be used. Accordingly, administration by inter alia, the parenteral, oral, sublingual, nasal and/or pulmonary routes are envisaged.

Wherein the small molecule signalling inhibitor is a PI3-kinase inhibitor, suitable examples include, but are not limited to, wortmannin, LY294002, demethoxyviridin, IC87114, NVP-BEZ235, BAY 80-6946, BKM120, GDC-0941, GDC-9080; including combinations thereof; and pharmaceutically acceptable salts, solvates, hydrates, stereoisomers, clathrates and prodrugs of any of the above.

Wherein the small molecule inhibitor is an AKT inhibitor, suitable examples include, but are not limited to, MK-2206, GSK690693, perifosine, PHT-427, AT7867, honokiol, PF-04691502; including combinations thereof; and pharmaceutically acceptable salts, solvates, hydrates, stereoisomers, clathrates and prodrugs of any of the above.

Wherein the small molecule signalling inhibitor is a taxane, suitable examples include, but are not limited to, paclitaxel and docetaxel; including combinations thereof; and pharmaceutically acceptable salts, solvates, hydrates, stereoisomers, clathrates and prodrugs of any of the above.

Wherein the small molecule inhibitor is an antimetabolite, suitable examples include, but are not limited to, methotrexate, 5-fluorouracil, capecitabin, cytosinarabinoside (Cytarabin), gemcitabine, 6-thioguanin, pentostatin, azathioprin, 6-mercaptopurin, fludarabin and cladribin; including combinations thereof; and pharmaceutically acceptable salts, solvates, hydrates, stereoisomers, clathrates and prodrugs of any of the above. Gemcitabine is an especially preferred antimetabolite. By way of example, gemcitabine may be administered at a dose (per administration) of 800-1200 mg/m$^2$, preferably 900-1100 mg/m$^2$, for example about 1000 mg/m$^2$, or 1000 mg/m$^2$. It is envisaged that gemcitabine may be especially effective due to the inhibition of myeloid suppressor cells, which can form an immunosuppressive 'shield' around certain cancer cell types; this is particularly relevant to the treatment of pancreatic cancer.

Wherein the small molecule signalling inhibitor is an alkylating agent, suitable examples include, but are not limited to, mechlorethamine, cyclophosphamide, ifosfamide, trofosfamide, melphalan (L-sarcolysin), chlorambucil, hexamethylmelamine, thiotepa, busulfan, carmustine (BCNU), streptozocin (streptozotocin), dacarbazine (DTIC; dimethyltriazenoimidazol ecarboxamide) temozolomide and oxaliplatin; including combinations thereof; and pharmaceutically acceptable salts, solvates, hydrates, stereoisomers, clathrates and prodrugs of any of the above. Cyclophosphamide and oxaliplatin are especially preferred alkylating agents. By way of example, oxaliplatin may be administered at a dose (per administration) of 65-105 mg/m$^2$, preferably 75-95 mg/m$^2$, for example about 85 mg/m$^2$, or 85 mg/m$^2$. By way of example, cyclophosphamide may be administered at a dose (per administration) of up to 1800 mg/m$^2$, for example 400-1800 mg/m$^2$.

Wherein the small molecule signalling inhibitor is a cell cycle inhibitor, suitable examples include, but are not limited to, Epothilone, Vincristine, Vinblastine, UCN-01, 17AAG, XL844, CHIR-124, PF-00477736, CEP-3891, Flavopiridol, berberine, P276-00, terameprocol, isoflavone daidzein, BI2536, BI6727, GSK461364, Cyclapolin, ON-01910, NMS-P937, TAK-960, Ispinesib, Monastrol, AZD4877, LY2523355, ARRY-520, MK-0731, SB743921, GSK923295, Lonafarnib, proTAME, Bortezomib, MLN9708, ONX0912, CEP-18770; including combinations thereof; and pharmaceutically acceptable salts, solvates, hydrates, stereoisomers, clathrates and prodrugs of any of the above; particularly suitable examples of cell cycle inhibitors include, but are not limited to, Hespaeradin, ZM447439, VX-680, MLN-8054, PHA-739358, AT-9283, AZD1152, MLN8237, ENMD2076, SU6668; including combinations thereof; and other inhibitors of Aurora kinases; and pharmaceutically acceptable salts, solvates, hydrates, stereoisomers, clathrates and prodrugs of any of the above.

According to a second aspect of the invention, there is provided a diagnostic test for monitoring the response of a subject having a tumour/cancer to a first treatment phase in which a subject is administered naltrexone or an analogue thereof; comprising analysing a sample obtained from the subject who is, or has been, undergoing said first treatment phase, to determine whether:

(a) BAD protein is upregulated and/or phosphorylated AKT protein is downregulated, (b) BAD protein is substantially localised to the mitochondria, and/or (c) BAD protein is not substantially in a phosphorylated state;

wherein, if they are, there is a positive indication of the subject to be suitable to undertake a second treatment phase, comprising administration of a small molecule signalling inhibitor selected from the group consisting of PI3-kinase inhibitors, AKT inhibitors, taxanes, antimetabolites, alkylating agents and cell cycle inhibitors.

The above observations are all positive indicators of the anti-apoptotic activity of BAD protein activity being stimulated through priming with LDN.

According to said second aspect, preferably the naltrexone or the analogue thereof is to be administered in the first treatment phase to the subject at a "low" dose, less than 0.5 mg/kg, preferably less than 0.2 mg/kg, more preferably between 0.01 mg/kg and 0.08 mg/kg, even more preferably between 0.03 mg/kg and 0.06 mg/kg, most preferably between 0.04 mg/kg and 0.05 mg/kg. The composition can be administered in any conventional way. Administration can be by oral or parenteral administration, preferably oral administration. However, other routes of administration are also envisaged. Said first treatment phase is preferably for administration for between 1 and 7 days, more preferably between 1 and 4 days, most preferably between 1 and 2 days; "day" meaning a continuous period of 24 hours. Naltrexone is preferably administered daily (at the above doses) during the first treatment phase.

Further according to said second aspect, upregulation of BAD protein and/or downregulation of phosphorylated AKT protein respectively, if present in cells from a sample obtained from the subject, may be determined. Quantitation of specific protein levels in one or more cells in a sample taken from the subject may be performed by any suitable method known in the art, including semi-quantitative methods. Such suitable methods include, but are not limited to, quantitative western blot, enzyme-linked immunosorbant assay (ELISA), mass spectrometry (in particular matrix-assisted laser desorption/ionisation (MALDI) mass spectrometry), and suitable derivatives and combinations of the above; methods whereby one or more identifiable fragments of the protein are quantified are also envisaged and within the purview of the invention. Upregulation and/or downregulation are to be determined relative to a control comprising one or more untreated and/or unstimulated cells (i.e. in a basal state) of the same tissue type, when measured under analogous conditions, preferably in a sample taken from the subject prior to the first treatment phase.

Further according to said second aspect, the subcellular localisation of BAD protein in cells from a sample obtained from the subject may be determined. This may be performed using any suitable method in the art, including, but not limited to immunohistochemistry, immunocytochemistry, and suitable derivatives and combinations of the above. BAD protein may be considered "substantially localised" to the mitochondria when the quantity of BAD protein within the volume of, or proximal to, the mitochondria is increased when compared with an untreated and/or unstimulated cell (i.e. in a basal state) of the same tissue type, when measured under otherwise analogous conditions; preferably in a sample taken from the subject prior to the first treatment phase.

Further according to said second aspect, the phosphorylation state of BAD protein in cells of a tumour/cancer may be determined. This may be performed using any suitable method in the art. Methods whereby an increase in the molecular weight of BAD protein resulting from the presence of one or more phosphate groups is detected and/or specific recognition of BAD protein when in a phosphorylated state (for example by an antibody) is elicited, are envisaged in particular; the absence of these occurrences indicating that BAD protein is not substantially in a phosphorylated state. Such methods include eastern blotting and suitable derivatives thereof. Preferably, the phosphorylation state of BAD is compared with a control comprising untreated and/or unstimulated cells (i.e. in a basal state) of the same tissue type, in a sample taken from the subject prior to the first treatment phase.

Further according to said second aspect, there is preferably a recovery phase between the first and second treatment phases, if there is a positive indication of the subject to be suitable to undertake the second treatment phase. Said recovery phase, in which there is no administration of either the naltrexone (or the analogue thereof) or the small molecule signalling inhibitor is for preferably at least 1 day, and more preferably at least 2 days. Alternatively, the recovery phase may be between 24 and 48 hours, 24 and 36 hours, or 24 and 30 hours. The features of said second treatment phase are dependent on the small molecule signalling inhibitor to be used, however administration is preferably daily, for at least 1 day.

Further according to said second aspect, preferably the small molecule signalling inhibitor is selected from the group consisting of antimetabolites and alkylating agents. The small molecule signalling inhibitor can be administered in any conventional way, the method of administration being largely dependent on the small molecule signalling inhibitor to be used. Accordingly, administration by inter alia, the parenteral, oral, sublingual, nasal and/or pulmonary routes is envisaged.

Wherein the small molecule signalling inhibitor is a PI3-kinase inhibitor, suitable examples include, but are not limited to, wortmannin, LY294002, demethoxyviridin, IC87114, NVP-BEZ235, BAY 80-6946, BKM120, GDC-0941, GDC-9080; including combinations thereof; and pharmaceutically acceptable salts, solvates, hydrates, stereoisomers, clathrates and prodrugs of any of the above.

Wherein the small molecule inhibitor is an AKT inhibitor, suitable examples include, but are not limited to, MK-2206, GSK690693, perifosine, PHT-427, AT7867, honokiol, PF-04691502; including combinations thereof; and pharmaceutically acceptable salts, solvates, hydrates, stereoisomers, clathrates and prodrugs of any of the above.

Wherein the small molecule signalling inhibitor is a taxane, suitable examples include, but are not limited to, paclitaxel and docetaxel; including combinations thereof; and pharmaceutically acceptable salts, solvates, hydrates, stereoisomers, clathrates and prodrugs of any of the above.

Wherein the small molecule inhibitor is an antimetabolite, suitable examples include, but are not limited to, methotrexate, 5-fluorouracil, capecitabin, cytosinarabinoside (Cytarabin), gemcitabin, 6-thioguanin, pentostatin, azathioprin, 6-mercaptopurin, fludarabin and cladribin; including combinations thereof; and pharmaceutically acceptable salts, solvates, hydrates, stereoisomers, clathrates and prodrugs of any of the above. Gemcitabine is an especially preferred antimetabolite.

Wherein the small molecule signalling inhibitor is an alkylating agent, suitable examples include, but are not limited to, mechlorethamine, cyclophosphamide, ifosfamide, trofosfamide, melphalan (L-sarcolysin), chlorambucil, hexamethylmelamine, thiotepa, busulfan, carmustine (BCNU), streptozocin (streptozotocin), dacarbazine (DTIC; dimethyltriazenoimidazolecarboxamide) temozolomide and oxaliplatin; including combinations thereof; and pharmaceutically acceptable salts, solvates, hydrates, stereoisomers, clathrates and prodrugs of any of the above. Cyclophosphamide and oxaliplatin are especially preferred alkylating agents.

Wherein the small molecule signalling inhibitor is a cell cycle inhibitor, suitable examples include, but are not limited to, Epothilone, Vincristine, Vinblastine, UCN-01, 17AAG, XL844, CHIR-124, PF-00477736, CEP-3891, Flavopiridol, berberine, P276-00, terameprocol, isoflavone daidzein, BI2536, BI6727, GSK461364, Cyclapolin, ON-01910, NMS-P937, TAK-960, Ispinesib, Monastrol, AZD4877, LY2523355, ARRY-520, MK-0731, SB743921, GSK923295, Lonafarnib, proTAME, Bortezomib, MLN9708, ONX0912, CEP-18770; including combinations thereof; and pharmaceutically acceptable salts, solvates, hydrates, stereoisomers, clathrates and prodrugs of any of the above; particularly suitable examples of cell cycle inhibitors include, but are not limited to, Hespaeradin, ZM447439, VX-680, MLN-8054, PHA-739358, AT-9283, AZD1152, MLN8237, ENMD2076, SU6668; including combinations thereof; and other inhibitors of Aurora kinases; and pharmaceutically acceptable salts, solvates, hydrates, stereoisomers, clathrates and prodrugs of any of the above.

According to a third aspect of the invention, there is provided an in vitro method of testing a small molecule signalling inhibitor for efficacy in the treatment of a tumour/cancer when for use in combination with naltrexone or an analogue thereof; comprising administering the small molecule signalling inhibitor, selected from the group consisting of PI3-kinase inhibitors, AKT inhibitors, taxanes, antimetabolites, alkylating agents and cell cycle inhibitors, concurrently with and/or after the naltrexone or the analogue thereof to cells of the tumour/cancer, and analysing a sample comprising one or more of said cells to determine whether:
(a) BAD protein is upregulated and/or phosphorylated AKT protein is downregulated,
(b) BAD protein is substantially localised to the mitochondria, and/or
(c) BAD protein is not substantially in a phosphorylated state;
wherein, if they are, there is a positive indication of the efficacy of the small molecule signalling inhibitor.

According to a fourth aspect of the invention, there is provided a pharmaceutical composition comprising naltrexone or an analogue thereof, for use in a method of testing a small molecule signalling inhibitor for efficacy in the treatment of a tumour/cancer when to be used in combination with the naltrexone or the analogue thereof, said method comprising administering the small molecule signalling inhibitor, selected from the group consisting of PI3-kinase inhibitors, AKT inhibitors, taxanes, antimetabolites, alkylating agents and cell cycle inhibitors, concurrently with and/or after the naltrexone or the analogue thereof to a subject having a tumour/cancer, and analysing a sample comprising one or more cells of the tumour/cancer to determine whether:
(a) BAD protein is upregulated and/or phosphorylated AKT protein is downregulated,
(b) BAD protein is substantially localised to the mitochondria, and/or
(c) BAD protein is not substantially in a phosphorylated state;
wherein, if they are, there is a positive indication of the efficacy of the small molecule signalling inhibitor agent.

According to said third and fourth aspects, upregulation of BAD protein and/or downregulation of phosphorylated AKT protein respectively, if present in cells of a tumour/cancer (when from a sample obtained from the subject, according to the fourth aspect), may be determined. Quantitation of specific protein levels in one or more cells in a sample taken from the subject may be performed by any suitable method known in the art, including semi-quantitative methods. Such suitable methods include, but are not limited to, quantitative western blot, enzyme-linked immunosorbant assay (ELISA), mass spectrometry (in particular matrix-assisted laser desorption/ionisation (MALDI) mass spectrometry), and suitable derivatives and combinations of the above; methods whereby one or more identifiable fragments of the protein are quantified are also envisaged and within the purview of the invention. Upregulation and/or downregulation are to be determined relative to a control comprising one or more untreated and/or unstimulated cells (i.e. in a basal state) of the same tissue type, when measured under analogous conditions (according to the fourth aspect, this is preferably in a sample taken from the subject prior to the administration of the naltrexone or the analogue thereof and the small molecule signalling inhibitor).

Further according to said third and fourth aspects, the subcellular localisation of BAD protein in cells of a tumour/cancer (when from a sample obtained from the subject, according to the fourth aspect) may be determined. This may be performed using any suitable method in the art, including, but not limited to immunohistochemistry, immunocytochemistry, and suitable derivatives and combinations of the above. preferably BAD protein is to be considered "substantially localised" to the mitochondria when the quantity of BAD protein within the volume of, or proximal to, the mitochondria is increased when compared with an untreated and/or unstimulated cell (i.e. in a basal state) of the same tissue type, when measured under otherwise analogous conditions (according to the fourth aspect, this is preferably in a sample taken from the subject prior to the administration of the naltrexone or the analogue thereof and the small molecule signalling inhibitor)

Further according to said third and fourth aspects, the phosphorylation state of BAD protein in cells of a tumour/cancer (when from a sample obtained from the subject, according to the fourth aspect) may be determined. This may be performed using any suitable method in the art. Methods whereby an increase in the molecular weight of BAD protein resulting from the presence of one or more phosphate groups is detected and/or specific recognition of BAD protein when in a phosphorylated state (for example by an antibody) is elicited, are envisaged in particular; the absence of these occurrences indicating that BAD protein is not substantially in a phosphorylated state. Such methods include eastern blotting and suitable derivatives thereof. According to said fourth aspect, preferably, the phosphorylation state of BAD is compared with a control comprising untreated and/or unstimulated cells (i.e. in a basal state) of the same tissue type, in a sample taken from the subject prior to administration of the naltrexone or the administration of the naltrexone or the analogue thereof and the small molecule signalling inhibitor.

According to said fourth aspect, preferably the naltrexone or the analogue thereof is to be administered in the first treatment phase to the subject at a "low" dose, less than 0.5 mg/kg, preferably less than 0.2 mg/kg, more preferably between 0.01 mg/kg and 0.08 mg/kg, even more preferably between 0.03 mg/kg and 0.06 mg/kg, most preferably between 0.04 mg/kg and 0.05 mg/kg.

Further according to said third and fourth aspects, preferably the small molecule signalling inhibitor is selected from the group consisting of antimetabolites and alkylating agents According to a further aspect of the invention, there is provided a method of treating or preventing a tumour/cancer in a subject in need of prevention or treatment thereof, said method comprising administering a therapeutically effective amount of naltrexone or an analogue thereof and a small molecule signalling inhibitor, said method having the same optional and preferred features as are applicable to the first aspect of the invention.

According to all aspects of the invention, it is to be noted that the tumours/cancers to be treated are not in any way limited. Accordingly, the treatment of any condition comprising a mass of tissue resulting from excessive cell growth, proliferation and/or survival, either benign (noncancerous) or malignant (cancerous) is envisaged, including pre-cancerous lesions. Therefore, examples include, but are not limited to, tumours/cancers comprising carcinoma, lymphoma, blastoma, sarcoma, and leukaemia; more particular examples of such tumours/cancers include, but are not limited to, those comprising squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, liver cancer, bladder cancer, hepatoma, breast cancer, colon cancer, colorectal cancer, endometrial or uterine carcinoma, salivary gland carcinoma, kidney cancer, liver cancer, prostate cancer, melanoma, vulval cancer, thyroid cancer, hepatic carcinoma and various types of head and neck cancers. In one preferred embodiment of the first aspect of the invention, however, the cancer comprises lung cancer, colorectal cancer, glioma or pancreatic cancer; more preferably the cancer comprises lung cancer or colorectal cancer, as demonstrated by Example 1. Wherein the small molecule inhibitor is gemcitabine (according to the first aspect of the invention), use in the treatment of pancreatic cancer is especially preferred.

All documents referred to above are incorporated herein by reference.

The invention is now illustrated by the following non-limiting Examples.

EXAMPLES

Example 1

To study the effect of each agent on cell growth, cells growing exponentially were added to 96-well plates at a density of $3 \times 10^4$/well. Drugs were then added to the wells, ensuring an equal volume of 200 µl across the plate. Cell number was measured at 72 hr using a standard methylthiazoletetrazolium (MTT)-based assay without modifications. Briefly, MTT was added to each well to give a working concentration of 0.4 mg/ml, and plates returned to the incubator for a further 1 hr. After this time, the medium was aspirated off, 200 μl of DMSO was then added to each well and plates agitated gently for 5 min before measuring optical density at 540 nm in each well. The effect of recovery, where a wash step was included, was studied by removing naltrexone-containing medium and replacing this with fresh drug-free medium after 48 hr, before assessing cell number at the 72 hr time-point. Cell counting was performed by under light microscopy using staining with trypan blue to aid the discrimination of dead/dying cells. See description of FIGS. 1 and 2.

Example 2

Cells were treated with 10 μM naltrexone (NTX) or 10 nM naltrexone (LDN) for 48 hr before they were harvested, and total cellular protein was solubilised in lysis buffer and resolved by Tris-glycine electrophoresis using a 4-12% bis-tris gradient-gel. Following transfer of proteins to 0.45-lm nitrocellulose membranes, blocking was performed in 5% (w/v) nonfat milk in TTBS [0.5% (v/v) Tween-20 in TBS (50 mM Tris, 150 mM NaCl, pH 8.0)]. Primary antibody probing for the protein specified in the figure were performed overnight at 4° C. before secondary probing using horseradish peroxidase-conjugated anti-species IgG1. Bands were visualised by the ECL-plus detection system. Densitometry analysis was performed using proprietary analysis software. RNA was extracted from these cells for gene expression analysis. RNA was purified by Trizol, followed by precipitation with isopropanol. The RNA pellet was washed in 70% (v/v) ethanol, air dried, resuspended in RNase-free water. Biotinylated cRNA was generated from 100 ng total RNA using the Illumina TotalPrep RNA Amplification Kit (Applied Biosystems, Warrington, UK) according to manufacturer's instructions. Equal amounts (750 ng) of cRNA were hybridised to the Illumina human HT12-v3 arrays for 18 hr and subsequently processed according to manufacturer's instructions before scanning on an Illumina BeadArray Reader. The image data were processed using default values in GenomeStudio v2009.1 with imputation of missing data, before loading onto GeneSpring v9.0 for data normalisation and filtering. Further analysis was performed using Excel. See description of FIGS. 3 and 4.

Example 3

HCT116 (human colon cancer) cells were cultured in standard culture medium following a treatment schedule consisting of two phases. Each phase lasted 2 days (48 h). Cells were reset at a concentration of 1×10^4 cells/ml and allowed to adhere to culture plates before addition of drugs as part of the first phase of treatment. Cells were either untreated or treated with 10 nM of naltrexone and maintained in a humidified atmosphere with 5% CO2 in air at 37 C. After 2-days, media were gently aspirated from each of the wells, and fresh media added. As part of the second phase of treatment, either naltrexone (10 nM), cyclophosphamide (10 uM), gemcitabine (1 uM) or oxaliplatin (1 uM) was added after the cells were drug-free for approximately 15 minutes. After 2 days, cells were harvested by trypsin and cell number and viability for each sample assessed by cell counting using trypan blue. Results are displayed in FIG. 5: U-U: untreated for 96 h; L-L: LDN for 96 h; U-C: untreated for 48 h then cyclophosphamide for 48 h; L-C: LDN for 48 h then cyclophosphamide for 48 h; U-G: untreated for 48 h then gemcitabine for 48 h; L-G LDN for 48 h then gemcit- abine for 48 h; U-O: untreated for 48 h then oxaliplatin for 48 h; L-O: LDN for 48 h then oxaliplatin for 48 h.

REFERENCES

Berkson, B. M., D. M. Rubin, and A. J. Berkson. 2009. Revisiting the ALA/N (alpha-lipoic acid/low-dose naltrexone) protocol for people with metastatic and nonmetastatic pancreatic cancer: a report of 3 new cases. *Integr Cancer Ther* 8:416-422.

Danial N. N., Gramm C. F., Scorrano L, Zhang C. Y., Krauss S, Ranger A. M et al. 2003. BAD and glucokinase reside in a mitochondrial complex that integrates glycolysis and apoptosis. *Nature.* 424: 952-956.

Danial, N. N. 2009. BAD: undertaker by night, candyman by day. *Oncogene.* 27: S53-S70

Donahue, R. N., P. J. McLaughlin, and I. S. Zagon. 2011a. Low-dose naltrexone suppresses ovarian cancer and exhibits enhanced inhibition in combination with cisplatin. *Experimental Biology and Medicine* 236:883-895

Donahue, R. N., P. J. McLaughlin, and I. S. Zagon. 2011b. Low-dose naltrexone targets the opioid growth factoropioid growth factor receptor pathway to inhibit cell proliferation: mechanistic evidence from a tissue culture model. *Experimental Biology and Medicine* 236:1036-1050.

Hytrek, S. D., P. J. McLaughlin, C. M. Lang, and I. S. Zagon. 1996. Inhibition of human colon cancer by intermittent opioid receptor blockade with naltrexone. *Cancer letters* 101:159-164.

Rahn, K. A., P. J. McLaughlin, and I. S. Zagon. 2011. Prevention and diminished expression of experimental autoimmune encephalomyelitis by low dose naltrexone (LDN) or opioid growth factor (OGF) for an extended period: therapeutic implications for multiple sclerosis. *Brain research.*

Smith, J. P., S. I. Bingaman, F. Ruggiero, D. T. Mauger, A. Mukherjee, C. O. McGovern, and I. S. Zagon. 2011. Therapy with the opioid antagonist naltrexone promotes mucosal healing in active Crohn's disease: a randomized placebo-controlled trial. *Dig Dis Sci* 56:2088-2097.

Zagon, I. S., and P. J. McLaughlin. 1983. Naltrexone modulates tumour response in mice with neuroblastoma. *Science* 221:671.

The invention claimed is:

1. A method of treating a subject having colon cancer comprising administering to the subject in a first treatment phase naltrexone at a dose of between 0.01 mg/kg and 0.08 mg/kg, followed by a recovery phase; wherein, following the recovery phase, a small molecule signalling inhibitor selected from the group consisting of gemcitabine, cyclophosphamide and oxaliplatin is to be administered to the subject in a second treatment phase; the recovery phase being characterized by the absence of administration of the naltrexone and the small molecule signalling inhibitor wherein the colon cancer is treated.

2. The method according to claim 1, wherein said first treatment phase is for administration for between 1 and 7 days, between 1 and 4 days, or between 1 and 2 days.

3. The method according to claim 1, wherein said second treatment phase is for daily administration for at least 1 day.

4. The method according to claim 1, wherein said recovery phase is for at least 1 day, or at least 2 consecutive days.

5. The method according to claim 1, wherein the small molecule signalling inhibitor is gemcitabine.

6. The method according to claim 1, wherein the small molecule signalling inhibitor is an alkylating agent selected from oxaliplatin or cyclophosphamide.

7. A diagnostic test for monitoring the response of a subject having colon cancer to a first treatment phase in which a subject is administered naltrexone at a dose of between 0.01 mg/kg and 0.08 mg/kg; comprising
   analyzing a sample obtained from the subject who is, or has been, undergoing said first treatment phase, to determine that:
   (a) Bcl-2-associated death (BAD) protein is upregulated and/or phosphorylated AKT protein is downregulated,
   (b) BAD protein is substantially localized to the mitochondria, and/or
   (c) BAD protein is not substantially in a phosphorylated state;
   which indicates there is a positive indication of the subject to be suitable to undertake a second treatment phase, comprising administration of a small molecule signalling inhibitor selected from the group consisting of gemcitabine, cyclophosphamide or oxaliplatin.

8. A diagnostic test according to claim 7, wherein said upregulation, downregulation, localization and/or phosphorylation state is assessed relative to a control comprising analysis of a sample taken from the subject prior to the first treatment phase.

9. A diagnostic test according to claim 7, wherein said first treatment phase is for administration for between 1 and 7 days, or between 1 and 4 days, or between 1 and 2 days.

10. A diagnostic test according to claim 7, wherein the small molecule signalling inhibitor is gemcitabine.

11. A diagnostic test according to claim 7, wherein the small molecule signalling inhibitor is an alkylating agent selected from oxaliplatin or cyclophosphamide.

12. An in vitro method of testing a small molecule signalling inhibitor for efficacy in the treatment of colon cancer in combination with naltrexone, wherein naltrexone is administered at a dose of between 0.01 mg/kg and 0.08 mg/kg, comprising administering the small molecule signalling inhibitor selected from the group consisting of gemcitabine, cyclophosphamide and oxaliplatin, concurrently with and/or after the naltrexone to cells of the colon cancer, and analyzing a sample comprising one or more of said cells to determine that:
   (a) Bcl-2-associated death (BAD) protein is upregulated and/or phosphorylated AKT protein is downregulated,
   (b) BAD protein is substantially localized to the mitochondria, and/or
   (c) BAD protein is not substantially in a phosphorylated state;
   which indicates there is a positive indication of the efficacy of the small molecule signalling inhibitor agent.

13. A method of testing a small molecule signalling inhibitor for efficacy in the treatment of colon cancer, said method comprising administering the small molecule signalling inhibitor selected from the group consisting of gemcitabine, cyclophosphamide or oxaliplatin concurrently with and/or after administering naltrexone to a subject having colon cancer at a dose of between 0.01 mg/kg and 0.08 mg/kg, and analyzing a sample comprising one or more cells of the colon cancer to determine that:
   (a) Bcl-2-associated death (BAD) protein is upregulated and/or phosphorylated AKT protein is downregulated,
   (b) BAD protein is substantially localized to the mitochondria, and/or
   (c) BAD protein is not substantially in a phosphorylated state;
   which indicates there is a positive indication of the efficacy of the small molecule signalling inhibitor agent.

* * * * *